United States Patent [19]

Lang

[11] Patent Number: 4,883,080
[45] Date of Patent: Nov. 28, 1989

[54] COMBINATION NOZZLE AND DENTAL FLOSS ASSEMBLY FOR ORAL HYGIENE FLUSHING APPARATUS

[76] Inventor: Dennis R. Lang, 12905 Mapleview St. Apt. 5-145, Lakeside, Calif. 92040

[21] Appl. No.: 228,494

[22] Filed: Aug. 5, 1988

[51] Int. Cl.$^4$ ............................................. A61C 15/00
[52] U.S. Cl. ................................... 132/322; 128/62 A
[58] Field of Search ....................... 132/323, 322, 326; 433/161; 128/62 A

[56] References Cited

U.S. PATENT DOCUMENTS

| | | | |
|---|---|---|---|
| 4,031,908 | 6/1977 | Ting | 132/322 |
| 4,319,595 | 3/1982 | Ulrich | 132/326 |

Primary Examiner—Robert Peshock
Attorney, Agent, or Firm—Charles C. Logan, II

[57] ABSTRACT

A combination nozzle and dental floss assembly formed of two major components fixedly secured to each other. One component is an elongated tubular member that functions as a nozzle and which has a curved tip portion at its top end. The bottom end of the tubular member has an attachment head for detachably connecting it to the oral hygiene flushing apparatus. An inlet port is formed in the bottom end of the tubular member and an outlet port is formed at its top end. The second component is a panel member that extends laterally from the tubular member and it has a finger member whose tip is oriented a predetermined spaced distance from the outlet port of the tubular member. A spool of dental floss is detachably mounted upon the panel member and is covered by a cap. The dental floss is threaded inwardly through an aperture in the tubular member and outwardly through the outlet port across to the tip of the finger member and then wound around a boss member extending upwardly from the panel member.

7 Claims, 1 Drawing Sheet

COMBINATION NOZZLE AND DENTAL FLOSS ASSEMBLY FOR ORAL HYGIENE FLUSHING APPARATUS

BACKGROUND OF THE INVENTION

The invention relates to an oral hygiene device and more specifically to a combination nozzle and dental floss assembly that would be detachably connected to the oral hygiene flushing apparatus.

For the last ten years there has been an oral hygiene flushing apparatus on the market that uses elongated nozzles that are detachably secured thereto. It is the curved tip portion of the nozzle that is inserted into the users mouth to direct a flow of high pressure water into the spaces between the teeth and around the gums in order to throughly cleanse them. This is a highly important method of reducing plaque buildup on one's teeth. While this method has been of considerable benefit to the people using these devices, it is also strongly recommended that they floss their teeth. Since the dental floss is stored in a separate container and it may be in the medicine cabinet or drawer, quite often the person is too lazy to regularly floss their teeth.

It is an object of the invention to provide a novel combination nozzle and dental floss assembly that can be quickly and easily attached and detached to existing oral hygiene flushing apparatus.

It is also an object of the invention to provide a novel combination nozzle and dental floss assembly that eliminates the need to have separate devices for flushing the teeth and also flossing them.

It is another object of the invention to provide a novel combination nozzle and dental floss assembly that is economical to manufacture and market.

It is an additional object of the invention to provide a novel combination nozzle and dental floss assembly that can be used with existing oral hygiene flushing apparatus.

SUMMARY OF THE INVENTION

Applicant's combination nozzle and dental floss assemby has been designed to be used with conventional oral hygiene flushing apparatus that are presently marketed. Its structure combines the use of a common tubular nozzle with structure for supporting a dental floss assembly thereon. A conventional attachment head is formed on the bottom end of the tubular nozzle and a threading aperture is formed adjacent the top end thereof. A panel member extends laterally from the tubular nozzle and it has a finger member whose tip is oriented laterally spaced from but aligned with the outlet port of the top end of the tubular nozzle. A boss member extends upwardly from the panel member and it has a top wall surface upon which a spool having dental floss wound thereon is supported. A cap member having a slit in its side wall is frictionally engaged on the outer surface of the boss member.

The dental floss that is threaded through the slit in the side wall of the cap is directed inwardly through the threading aperture in the tubular nozzle and out through the outlet port. It is next wound around the notch in the tip of the finger member and finally wrapped a couple of turns around the tapered wall portion of the boss member. At this point the combination nozzle and dental floss assembly is ready for attachment to the oral hygiene flushing apparatus and it can be used to concurrently flush between the teeth of the user and also floss at the same time.

DESCRIPTION OF THE PREFERRED EMBODIMENT

Figure 1:
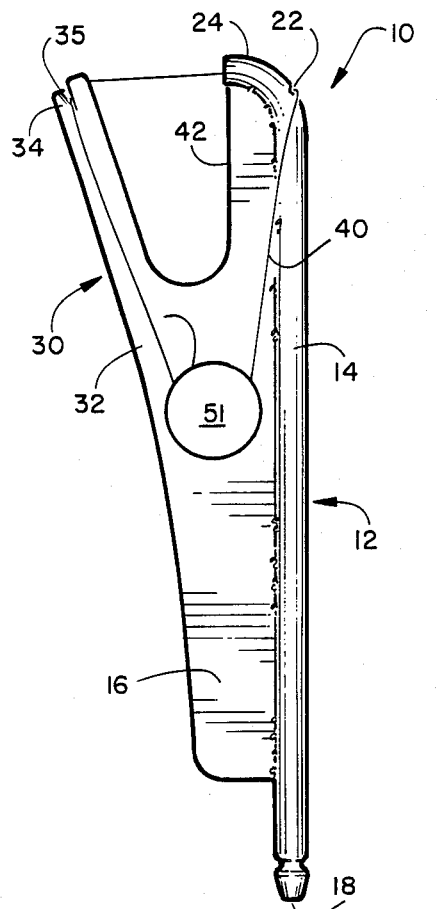
FIG. 1 is a front elevation view of the novel nozzle and dental floss assembly.
Figure 2:
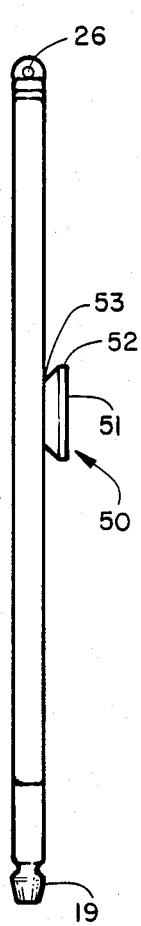
FIG. 2 is a side elevation view of the novel combination nozzle and dental floss assembly.
Figure 3:
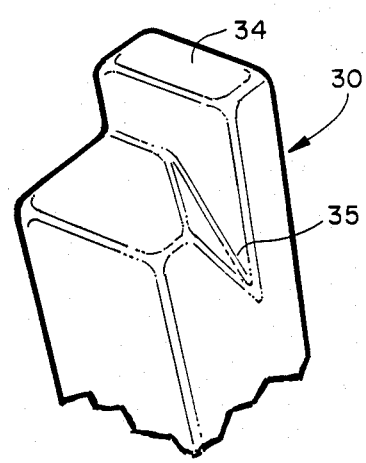
FIG. 3 is an enlarged partial view of the tip of the finger member.
Figure 4:
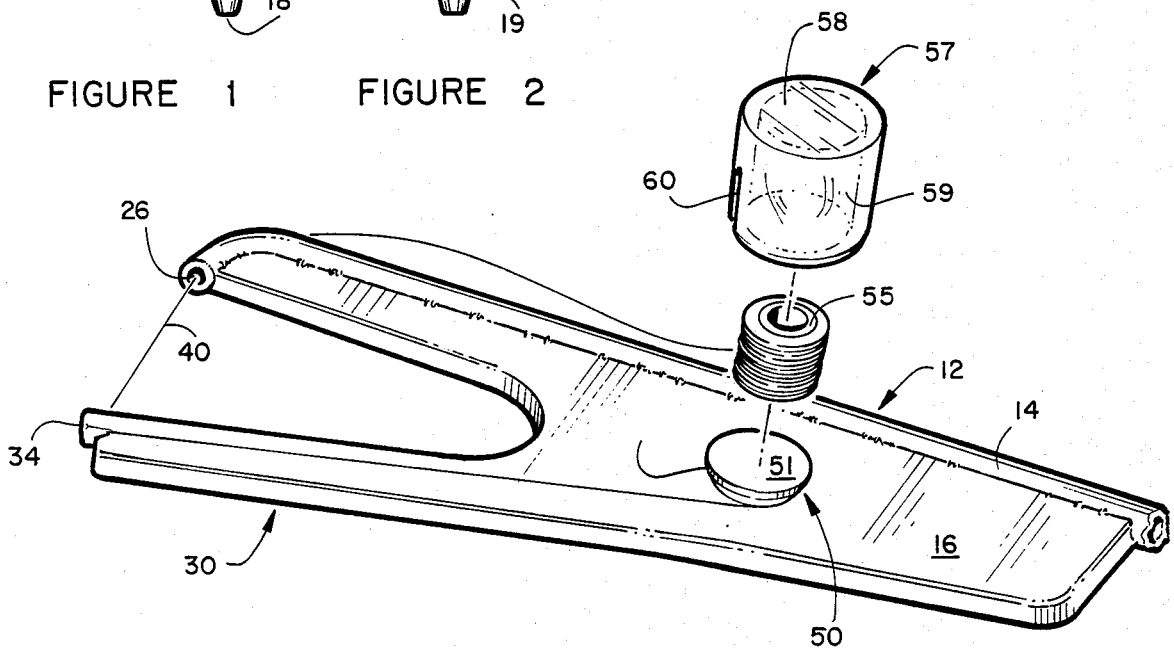
FIG. 4 is an exploded perspective view of the combination nozzle and dental floss assembly.

Applicant's novel combination nozzle and dental floss assembly for oral hygiene flushing apparatus will now be described by referring to FIGS. 1-4 of the drawing. The combination structure is generally designated numeral 10.

The combination structure 10 has a nozzle 12 formed from an elongated tubular member 14. A panel member 16 extends laterally therefrom.

Tubular member 14 has an inlet port 18 in its attachment head 19 formed at its bottom end. A threading aperture 22 is formed in the curved tip portion 24 at the top end of tubular member 14 and it has an outlet port 26.

Panel member 16 has a finger member 30 having a bottom end portion 32 and a tip 34. A notch 35 is formed in tip 34 for wedging the dental floss 40 therein. A cutout portion 42 provides an open space between tip 34 and outlet port 26. A boss member 50 extends upwardly from panel member 16 and it has a top wall 51, cylindrical side wall portion 52, and tapered wall portion 53. A spool 55 has dental floss 40 wound thereon and it would rest on top wall 51. A cap 57 having a top wall 58 and cylindrical side walls 59 has its inner diameter frictionally captured on cylindrical wall portion 52. A slit 60 allows the dental floss 40 to be threaded outwardly therefrom after which it is directed inwardly through threading aperture 22 and it exits tubular member 14 at outlet port 26.

What is claimed is:

1. A combination nozzle and dental floss assembly for oral hygiene flushing apparatus comprising:
    an elongated nozzle having an inlet port and an outlet port formed in its respective opposite ends: and
    a finger member having a bottom end and said bottom end is connected to said nozzle, said finger member having a tip that is spaced a predetermined distance from the outlet port of said nozzle; and
    means for detachably stringing a predetermined length of dental floss between the tip of said finger member end and the outlet port of said elongated nozzle.

2. A combination as recited in claim 1 wherein said nozzle is in the form of a tubular member.

3. A combination as recited in claim 2 wherein the inlet port end of said tubular member has an attachment head formed thereon for removably attaching it to an oral hygiene flushing apparatus.

4. A combination as recited in claim 3 wherein said tubular member has a curved tip portion at its outlet port end that is oriented toward the tip of said finger member.

5. A combination as recited in claim 4 wherein said finger member is part of a panel member extending laterally from said nozzle.

6. A combination as recited in claim 5 further comprising a spool having dental floss wound thereon and means for detachably mounting said spool on said panel member.

7. A combination as recited in claim 6 wherein said means for stringing the dental floss between the tip of said finger member and the outlet port of said nozzle comprises a threading aperture in said tubular member at a predetermined position which allows the dental floss to be threaded therethrough and out said outlet port.

* * * * *